(12) United States Patent
Stubbins et al.

(10) Patent No.: US 10,557,842 B2
(45) Date of Patent: *Feb. 11, 2020

(54) METHOD AND SYSTEM FOR ANALYSING A BLEND OF TWO OR MORE HYDROCARBON FEED STREAMS

(71) Applicant: INTERTEK GROUP PLC, London (GB)

(72) Inventors: Frederick J. Stubbins, London (GB); John Wade, London (GB); Paul Winstone, London (GB)

(73) Assignee: Intertek Group PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/178,051

(22) Filed: Nov. 1, 2018

(65) Prior Publication Data
US 2019/0064076 A1 Feb. 28, 2019

Related U.S. Application Data

(63) Continuation of application No. 15/039,481, filed as application No. PCT/GB2014/053586 on Dec. 2, 2014, now Pat. No. 10,145,802.

(30) Foreign Application Priority Data

Dec. 9, 2013 (GB) .................................. 1321677.5

(51) Int. Cl.
*G01N 21/79* (2006.01)
*G01N 31/22* (2006.01)
(Continued)

(52) U.S. Cl.
CPC ........... *G01N 33/2823* (2013.01); *C10G 7/10* (2013.01); *C10G 7/12* (2013.01); *C10G 75/00* (2013.01);
(Continued)

(58) Field of Classification Search
CPC . C10G 7/10; C10G 7/12; C10G 75/00; C10G 2300/1033; G01N 21/359;
(Continued)

(56) References Cited

U.S. PATENT DOCUMENTS 4,628,204 A 12/1986 Maes
4,843,247 A 6/1989 Yamazoe et al.
(Continued)

OTHER PUBLICATIONS

Asomaning, "Test Methods for Determining Asphaltene Stability in Crude Oils", Petroleum Science and Technology, vol. 21; Issue 3-4; pp. 581-590 (2003).
(Continued)

*Primary Examiner* — Renee Robinson
(74) *Attorney, Agent, or Firm* — Ajay A. Jagtiani; Miles & Stockbridge P.C.

(57) ABSTRACT

The invention relates to a method for analysing a blend of two or more hydrocarbon feed streams such as crude oils. These crude oils are blended in a facility such as a refinery. The method assesses the compatibility of a hydrocarbon feed in a blend to calculate the blend stability such that organic deposition is minimised. The method uses all of a plurality of hydrocarbon feeds to be blended for analysis. The method either selects a neat hydrocarbon feed, from a plurality of the hydrocarbon feeds included in a blend, as a titrant, wherein the or each other hydrocarbon in the hydrocarbon feed are used to make a pseudo-blend and titrating the pseudo-blend with said selected neat hydrocarbon feed for a plurality of different blend ratios. Alternatively the method involves preparing a reference hydrocarbon and making a blend from the plurality of hydrocarbon feeds and titrating the blend with the reference hydrocarbon. Measurements associated with the change in characteristics of the titrated blend are made and data recorded. The method then calculates, using said data, the stability of the blend.

10 Claims, 7 Drawing Sheets

(51) Int. Cl.
*G01N 21/83* (2006.01)
*G01N 33/28* (2006.01)
*C10G 75/00* (2006.01)
*C10G 7/10* (2006.01)
*C10G 7/12* (2006.01)
*G01N 21/3577* (2014.01)
*G01N 21/359* (2014.01)
*G01N 31/16* (2006.01)

(52) U.S. Cl.
CPC ....... *G01N 21/359* (2013.01); *G01N 21/3577* (2013.01); *G01N 21/79* (2013.01); *G01N 21/83* (2013.01); *G01N 31/22* (2013.01); *G01N 33/287* (2013.01); *G01N 33/2829* (2013.01); *G01N 33/2835* (2013.01); *G01N 33/2858* (2013.01); *C10G 2300/1033* (2013.01); *G01N 31/16* (2013.01)

(58) Field of Classification Search
CPC ........ G01N 21/79; G01N 21/83; G01N 31/16; G01N 31/22; G01N 33/2823; G01N 33/2835; G01N 33/2858; G01N 33/287
See application file for complete search history.

(56) References Cited

U.S. PATENT DOCUMENTS

| | | |
|---|---|---|
| 4,940,900 A | 7/1990 | Lambert |
| 5,871,634 A | 2/1999 | Wiche et al. |
| 5,997,723 A | 12/1999 | Wiche et al. |
| 7,618,822 B2 | 11/2009 | Nemana et al. |
| 7,813,894 B2 | 10/2010 | Prasad et al. |
| 7,833,407 B2 | 11/2010 | Brons et al. |
| 8,017,910 B2 | 9/2011 | Sharpe |
| 8,367,425 B1 | 2/2013 | Schabron et al. |
| 2005/0013740 A1 | 1/2005 | Mason et al. |
| 2010/0096552 A1 | 4/2010 | Sharpe |
| 2013/0161233 A1 | 6/2013 | Bennett et al. |
| 2013/0341241 A1 | 12/2013 | Respini et al. |

OTHER PUBLICATIONS

Stark et al., "New Method Prevents Desalter Upsets from Blending Incompatible Crudes", Oil and Gas Journal, Pennwell, Houston, TX, US; vol. 100; No. 11 pp. 89-91 (2002).
Search Report received in PCT Application No. PCT/GB2014/053586 dated Feb. 9, 2015.

| Blends | Crude001 | Crude002 | Crude003 | Crude004 | Crude005 | Crude006 | Crude007 | Crude008 | Crude... | Crude0nn | Crude101 | Crude102 | Crude103 | Crude104 | Crude1... | Crude1nn | Crude... | Crude... | Crude... | Crude... | Crude... | Crude... | Crudenn | API | Sulfur | TAN | Asphaltenes | P | N | A | Pour Point | TBP 65 | 100 | 150 | 200 | 250 | 300 | 350 | 370 | 475 | 525 | 565 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| 1nn01 | P | L | P | L | P | | L | P | | | | | | | | | | | | | | | | 39.8 | 0.3 | 0.5 | 0.3 | 45 | 35 | 20 | -20 | 6 | 13 | 22 | 30 | 39 | 48 | 57 | 60 | 75 | 81 | 84 |
| 1nn02 | L | L | L | L | P | | P | P | | | | | | | | | | | | | | | | 40.2 | 0.3 | 0.5 | 0.3 | 50 | 32 | 18 | -25 | 5 | 10 | 19 | 26 | 35 | 44 | 54 | 57 | 73 | 79 | 83 |
| 1nn03 | P | L | P | L | P | | P | L | | | | | | | | | | | | | | | | 41.3 | 0.2 | 0.5 | 0.3 | 52 | 45 | 3 | -29 | 8 | 15 | 26 | 34 | 43 | 53 | 62 | 65 | 80 | 85 | 88 |
| 1nn04 | P | L | P | L | P | | P | P | | | | | | | | | | | | | | | | 39.9 | 0.2 | 0.4 | 0.3 | 51 | 31 | 18 | -18 | 7 | 14 | 24 | 32 | 41 | 50 | 59 | 62 | 78 | 83 | 86 |
| 1nn05 | L | L | L | L | P | | H | P | | | | | | | | | | | | | | | | 40.0 | 0.2 | 0.5 | 0.3 | 48 | 24 | 28 | -16 | 7 | 14 | 24 | 32 | 41 | 51 | 60 | 63 | 79 | 84 | 87 |
| 1nn06 | | | | | | | P | | | | | | | P | | | | P | | P | | | | | | | | | | | | | | | | | | | | | |
| 1nn06 | | | | | | | P | | | | | | | | | | | | P | | | | | | | | | | | | | | | | | | | | | | |
| 1nn06 | | | | | | | | P | | | | | | | | | | | P | P | | | | | | | | | | | | | | | | | | | | | |
| 1nn06 | | | P | | | | | | | | | | | | | | P | P | P | | | | | | | | | | | | | | | | | | | | | | |
| 1nn06 | | | | | P | | | | | | | | | | | | | | P | | | | | | | | | | | | | | | | | | | | | | |
| 2nn01 | | | | | | | | | P | P | | | | | | P | | P | | | | | | | | | | | | | | | | | | | | | | | |
| 2nn02 | P | P | | P | P | | | | P | P | P | | P | | P | P | P | P | P | P | P | P | P | | | | | | | | | | | | | | | | | | |
| 2nn03 | | | | | | | | | | | | | | | | | | P | | | P | | | | | | | | | | | | | | | | | | | | |
| 2nn04 | | | | | | | | | | | | | | | | | | | | | | | | | | | | | | | | | | | | | | | | | |
| 2nn05 | | | | | | | | | | | P | | | | P | P | P | | P | P | P | P | P | | | | | | | | | | | | | | | | | | |

|  | Crude_01 | Crude_02 | Crude_03 | Crude_04 | Crude_05 |
|---|---|---|---|---|---|
| Min | 0% | 1% | 0% | 4% | 30% |
| Max | 52% | 13% | 8% | 38% | 90% |
| Average | 21% | 5% | 3% | 13% | 58% |
| Span | 52% | 13% | 8% | 34% | 60% |

| Blend Titration | Crude_01 | Crude_02 | Crude_03 | Crude_04 | Crude_05 | D0 Spectra / Observation | D0 Intertek Blending Algorithm | D24 Spectra / Observation | D24 Intertek Blending Algorithm | Comments from Microscopy |
|---|---|---|---|---|---|---|---|---|---|---|
| 111 | 52.1% | 3.3% | 3.3% | 11.4% | 30.0% | g | g | r | r |  |
| 112 | 44.7% | 2.8% | 2.8% | 9.8% | 40.0% | g | g | r | r |  |
| 113 | 37.2% | 2.3% | 2.3% | 8.1% | 50.0% | g | g | g | g |  |
| 114 | 29.8% | 1.9% | 1.9% | 6.5% | 60.0% | g | g | g | g |  |
| 115 | 22.3% | 1.4% | 1.4% | 4.9% | 70.0% | g | g | r | r |  |
| 121 | 1.7% | 8.6% | 1.7% | 37.9% | 50.0% | g | g | r | r |  |
| 122 | 1.4% | 6.9% | 1.4% | 30.3% | 60.0% | g | g | r | r |  |
| 123 | 1.0% | 5.2% | 1.0% | 22.8% | 70.0% | g | g | g | g |  |
| 124 | 0.7% | 3.4% | 0.7% | 15.2% | 80.0% | g | g | r | r |  |
| 125 | 0.3% | 1.7% | 0.3% | 7.6% | 90.0% | g | g | g | g |  |
| 131 | 50.9% | 1.3% | 3.8% | 14.0% | 30.0% | g | g | r | r |  |
| 132 | 43.6% | 1.1% | 3.3% | 12.0% | 40.0% | g | g | r | r |  |
| 133 | 36.4% | 0.9% | 2.7% | 10.0% | 50.0% | g | g | r | r |  |
| 134 | 29.1% | 0.7% | 2.2% | 8.0% | 60.0% | g | g | g | g |  |
| 135 | 21.8% | 0.5% | 1.6% | 6.0% | 70.0% | g | g | r | r |  |
| 141 | 40.0% | 13.3% | 8.3% | 8.3% | 30.0% | g | g | r | r |  |
| 142 | 34.3% | 11.4% | 7.1% | 7.1% | 40.0% | g | g | r | r |  |
| 143 | 28.6% | 9.5% | 6.0% | 6.0% | 50.0% | g | g | r | r |  |
| 144 | 22.9% | 7.6% | 4.8% | 4.8% | 60.0% | g | g | g | g |  |
| 145 | 17.1% | 5.7% | 3.6% | 3.6% | 70.0% | g | g | r | r |  |
| 151 | 3.7% | 11.1% | 3.7% | 31.5% | 50.0% | g | g | r | r |  |
| 152 | 3.0% | 8.9% | 3.0% | 25.2% | 60.0% | g | g | r | r |  |
| 153 | 2.2% | 6.7% | 2.2% | 18.9% | 70.0% | g | g | r | r |  |
| 154 | 1.5% | 4.4% | 1.5% | 12.6% | 80.0% | g | g | g | g |  |
| 155 | 0.7% | 2.2% | 0.7% | 6.3% | 90.0% | g | g | g | g |  |

METHOD AND SYSTEM FOR ANALYSING A BLEND OF TWO OR MORE HYDROCARBON FEED STREAMS

The invention relates to a method for assessing, measuring and calculating the stability of a blend of hydrocarbon feed streams, such as crude oil blends, and assessing the organic deposition from a blend. The invention also relates to a system and installation for assessing, measuring and calculating the stability of such a blend. In particular, the invention relates the assessment of organic deposition from a blend of crude oils.

Refinery margins are becoming challenged due to the rising cost of crude, increasingly stringent emissions regulations and refinery operating constraints, such as True Boiling Point (TBP), sulphur, density, Total Acid Number (TAN) etc.

To improve profit margins, heavier crudes are increasingly used to lower the overall cost of the crude blend and 'opportunity' crudes (e.g. heavy and "high acidic") are appealing feedstock. Unfortunately, blending opportunity crudes is known to result in a number of problems including: the deposition of asphaltenes and crystalline organics; processing difficulties due to the high solid content, sulphur content, asphaltenes, viscosity, stability and compatibility problems.

In addition to the aforementioned problems, less stable crude may more readily flocculate and precipitate organic materials immediately or over time (i.e. in storage). This is because the production of crude oil leads to it containing solids, liquid and gases. Therefore, the mixture can become more or less stable for a variety of factors including pressure, temperature, and blending.

Known systems and methods of analysing hydrocarbon feed streams include:

US 2013/0161233 appears to disclose a method of reducing the fouling propensity of a hydrocarbon feed stream by preparing a blend having specific properties of Total Base Number based on ASTM method S2896-11 and/or a P-value according to ASTM method D7060/09.

U.S. Pat. No. 5,997,723 appears to disclose blending two or more petroleum oils, any component of which may be an unprocessed crude oil or a processed oil derived from petroleum such that fouling and coking of equipment is minimised. The methods includes the assessment of the solubility blending number, S, for each oil.

U.S. Pat. No. 5,871,634 appears to disclose a method for blending two or more petroleum feed streams, wherein the insolubility number (IN) and blending number (SBN) are assessed for each feed stream.

U.S. Pat. No. 7,833,407 appears to disclose a method wherein a high solvency dispersive power (HDSP) crude is added to a blend of incompatible oils.

U.S. Pat. No. 7,813,894 appears to disclose a method and system that include assessment of various constituents in the crude, estimated model parameters, monitoring and predicting qualitative and quantitative performance and determining optimal dosage of chemical treatments.

U.S. Pat. No. 8,367,425 appears to disclose a method for determining the stability of asphaltenes using a series of sampling, measuring and monitoring steps.

U.S. Pat. No. 4,940,900 appears to disclose a means of determining the flocculation threshold of a petroleum product containing asphaltenes using radiation in the near infrared transmitted through a sample of the product in solution in a solvent in relation to the quantity of precipitant continuously-added to the sample.

U.S. Pat. No. 4,843,247 appears to disclose a method for determining an asphaltene content in a heavy hydrocarbon oil using a method that measures absorbance of a sample solution having dispersed therein asphaltene particles at two different wavelengths.

U.S. Pat. No. 7,618,822 appears to disclose a method for blending at least two hydrocarbon liquids, the method comprising determining the critical solvent power for each hydrocarbon liquid, determining the solvent power for each hydrocarbon liquid and blending the each crude oil into each other producing a crude oil blend wherein the solvent power of the crude oil blend is greater than the critical solvent power of the crude oil having the highest critical solvent power in the blend.

U.S. Pat. No. 8,017,910 appears to disclose a method of predicting the stability of a hydrocarbon process by obtaining samples from one or more process streams and measuring the actual stability and the near infrared spectral absorbance of those samples. A classification model is developed to identify sample subsets and correlation model is created using the stability and absorbance data by inserting that data into a mathematical function.

These known methods for assessing solubility and insolubility of asphaltenes use pure solvents and titrants such as toluene/1-methylnaphthalene and n-heptane/n-hexadecane. Insolubility/solubility limits are detected using optical density wherein single measurements use a single wavelength. Such methods assume that on blending, the solubility number of the mixture is calculated by volumetric proportional blending of the neat crude solubility number. The insolubility of the mixture is the maximum insolubility number of any single crude oil in the blend. Recognised laboratory methods have been used to support these approaches including:

ASTM D7157-09 Standard Test Method for Determination of Intrinsic Stability of Asphaltene-Containing Residues, Heavy Fuel Oils, and Crude Oils (n-Heptane Phase Separation; Optical Detection).

ASTM D7060-12 Standard Test Method for Determination of the Maximum Flocculation Ratio and Peptizing Power in Residual and Heavy Fuel Oils (Optical Detection Method).

ASTM D7112 Standard Test Method for Determining Stability and Compatibility of Heavy Fuel Oils and Crude Oils by Heavy Fuel Oil Stability Analyser (Optical Detection).

ASTM D7157 deposition point testing is carried out by taking three ratios of toluene to crude and titrating with n-heptane to determine the flocculation point for each neat crude. The flocculation points are plotted and regression lines drawn and the X-axis and Y-axis intercepts obtained. From the x and y intercepts the ASTM method D7157 gives FRmax (y-intercept) and Xmin (x-intercept). The S-value of an oil is 1+Xmin. The ASTM D7157 gives no further information on how to use these values, and merely states that: an oil with a low S-value is likely to undergo flocculation of asphaltenes when stressed (for example, extended heated storage) or blended with a range of other oils; and two oils each with a high S-value are likely to maintain asphaltenes in a peptized state and not lead to asphaltene flocculation when blended together.

U.S. Pat. Nos. 5,871,634 and 5,997,723 employ similar methodology to obtain the Insolubility Number (IN—y-intercept) and Solubility Blend Number (SBN—calculated from x-intercept) for the crude oil. Condensates and/or very stable (low asphaltene) crude oils are characterised by performing one heptane:toluene titration with a crude already characterised and the SBN is determined by differences therebetween. The SBN and IN can be used to predict the compatibility of crude oils when blending. If the blend SBN is greater than the blend IN, then the blend will be stable. If the blend SBN is less than the blend IN, then the blend will be unstable.

These existing methods for measuring asphaltenes are recorded over short periods of time and do not measure the effects of interactions over longer periods. Known systems and methods of assessing crude stability and determining the stability of blends from experimental data, and by calculation using various algorithms, focus on the titration in which the titrant is a pure material such as n-heptane. Using pure components, however, cannot be used to assess the interactions between crudes when blended. Known approaches assume that there is no interaction between the crudes in the mixture, furthermore U.S. Pat. No. 5,997,723 factors in a margin of 1.4 multiplied by the insolubility number of the highest insolubility number oil in the mixture, thus limiting the blends a refinery operator may select for blending.

Investigations suggest that combinations of resins and asphaltenes in neat crudes behave in different ways when in a blend with other crudes. The resins and asphaltenes interact chemically to affect crude blend stability. Crude oil is a colloidal system which changes during blending and whilst being thermodynamically unstable it may be kinetically stable.

SUMMARY OF THE INVENTION

Overall the invention relates to analysing a blend of two or more hydrocarbon feed streams such as crude oils for processing in a blending facility such as a refinery for assessing the compatibility of a hydrocarbon feed in a blend to calculate the blend stability for assessing organic deposition from said blend. The invention includes using all of a plurality of hydrocarbon feeds to be blended for analysis and during each titration. Measurements and data associated with the change in characteristics of the blend during titration is recorded. The invention calculates, using said data, the stability of the blend.

In one aspect, the invention resides in a method for analysing a blend of two or more hydrocarbon feed streams such as crude oils for processing in a blending facility such as a refinery for assessing the compatibility of a hydrocarbon feed in a blend to calculate the blend stability for assessing organic deposition from said blend, the method including: using all of a plurality of hydrocarbon feeds to be blended for analysis and either (i) selecting a neat hydrocarbon feed, from the plurality of hydrocarbon feeds to be included in a blend, as a titrant, wherein the or each other hydrocarbon in the hydrocarbon feed are used to make a pseudo-blend, or (ii) preparing a reference hydrocarbon and making a blend from the plurality of hydrocarbon feeds; titrating the pseudo-blend with said selected neat hydrocarbon for a plurality of different blend ratios or titrating the blend with the reference hydrocarbon; measuring and recording data associated with the change in characteristics of the titrated blend; and calculating, using said data, the stability of the blend. The measured and recorded data can be stored in a dataset on a device such as a ROM of a computer. The pseudo-blend can be one of a pair of hydrocarbon feeds being blended.

By using all of the neat hydrocarbon feeds that a refinery intends to blend and process a more accurate assessment of the blend stability can be made. Although the invention relates to blending hydrocarbon feed streams the invention hereinafter will be described, by way of example, in relation to crude oils. These crude oils are typically those available on a refinery slate. The slate determines which crudes are available for blending and the refinery constraints can determine which blends meet refinery operating criteria.

In contrast to known techniques, experiments and measurements use a neat crude as titrant, which is titrated into the pseudo-blend (a combination of the remaining crudes). Alternatively, a reference hydrocarbon can be prepared and used as a titrant, which is titrated in to a blend of the neat crudes from the hydrocarbon feedstream that a refinery wishes to process. Using a neat feed or crude, or a reference hydrocarbon, as the titrant provides a more accurate indication of the stability of a resulting blend. The neat crude can be sampled from a hydrocarbon feed, such as a crude oil storage container, that a refinery operator wishes to add to a blend. Samples are taken from the other crude or crudes that will form the rest of the blend—these samples are combined to form the pseudo-blend. To be clear, the term pseudo-blend is used to refer to a blend of all but one of the crude oils that will form a blend to be refined.

Measurement data can be obtained from titrating said pseudo-blend with the neat hydrocarbon feed over a period of time and/or over a range of temperatures and/or over a range of pressures. Taking such measurements enables the method to simulate refinery conditions.

Measurement data can be obtained from a Near Infra-Red (NIR) spectrum. The NIR spectrum can use wave numbers between 4 k cm$^{-1}$ and 10 k cm$^{-1}$. NIR measurements can be made with multiple wavelengths. Multiple wavelengths can be measured simultaneously. Inflection points can be validated by microscopy.

The plurality of hydrocarbon feeds selected for a blend, and the titrations therefrom, can use discrete samples, or sub-samples, to simulate refinery storage and processing conditions. The discrete samples can be prepared substantially simultaneously. Each sample can be taken from a single batch of neat crude. By way of example, a large sample of each crude oil on a slate is taken. Each batch can also be analysed. The NIR spectra of each crude, or batch of crude, can be measured.

One of the neat crudes is selected as a titrant for titration in to the remaining crudes (which combine to form a pseudo-blend). A plurality of pseudo-blends can be prepared as discrete samples. These can be sub-samples having a smaller volume that is prepared from the large samples of neat crudes. These can be prepared at substantially the same time. In other words, a plurality of pseudo-blends can be prepared as a series of sub-samples and stored, by way of example, in vials. Each sub-sample has a blend of different crudes. Each pseudo-blend can be titrated with a neat crude individually. By making individual titrations instead of progressive or continuous titrations the composition of the pseudo-blend is maintained. In this way, titration measurements can have a common reference because the composition of the sample remains substantially constant. Moreover, using discrete samples can provide a common reference when assessing the stability at different periods of times after the titration is complete. To be clear, a titration measurement for a given pseudo-blend will have the same composition whether 5% or 10% of neat crude is used as a titrant. The plurality of hydrocarbon feeds selected for a blend are selected to identify stable and unstable blends that overlap or extend beyond a refinery operating envelope. The method can assess the stability of a blend as the ratio of the crudes within the blend approaching the operating envelope. The envelope defines the operational limit of a blend facility.

Two or more hydrocarbon feed streams can be selected from a dataset having a record of the properties of each hydrocarbon feed stream, wherein the dataset includes a list of feasible and infeasible blends for a blending facility. The dataset can be a blend feasibility report.

The method can include quality tracking. Although a refiner can have a list, table or dataset including stable and unstable recipes, the available hydrocarbon feeds, crudes or similar feedstock varies in quality and regular monitoring is required. Similarly, new crudes can become available. The method can be used to validate the stability of blends within the blend feasibility report.

The method can monitor the characteristics of the or each hydrocarbon feed stream and, if the measured hydrocarbon feed stream falls outside a control limit. This can be a trigger for further blend evaluation. If a new hydrocarbon feed is to be included in the dataset, said hydrocarbon feed can be selected as the titrant.

A series of titration experiments can be carried out and blend stability can be calculated from regression analysis on the data. Data can be obtained from the dataset. The data can include the point of organic deposition of the blend titration and the associated ratio of each component of the blend and the titrant level. The regression analysis can be used to calculate a coefficient for each of the blend components.

In a titration experiment, pseudo component blends and titrant levels can be determined by the blend feasibility report, or dataset. Titrations can then be performed using discrete samples. By way of example, one vial per each day of analysis and blend ratio for spectroscopy and microscopy can be taken from the or each feedstream. Titrations can be assessed using non pre-processed NIR spectroscopy over the complete 4000-10000 cm-1 region. Changes in the combination region 4000-4800 cm-1 show changes due to physical and chemical phenomena (i.e. bonds forming and breaking). Changes in the higher wave number region from the 1st overtone upwards are also due to physical and chemical phenomena (i.e. increasing aggregate size). A true inflection point exhibits a distinct increase in absorbance throughout the whole spectrum.

The method can include a series of titration experiments that are carried out for stable and unstable blend recipes, and spectra measurements taken at the point of organic deposition for each blend are mapped on an aggregate plot such that the calculation of stable and unstable blends can be validated. Measurements are taken using NIR. Determining the stability and instability of a blend can involve measuring the inflection points during the blend titration. A regression analysis is performed to acquire coefficients for each of the blend components which reflect the point of organic deposition for all ratios tested. These coefficients can then be proportionally blended using the blend evaluation report to ascertain whether a selected blend ratio is stable or unstable.

Measurements are taken with the pseudo component ratios at the point of inflection for each blend as the X block. To be clear, these are the variables in the regression analysis and are the percentages of crudes in the pseudo component at the point of titration. In the regression analysis the X block is regressed upon the corresponding titrant level, or the Y block, which is the percentage of crudes in the pseudo component at the point of titration. Stability and instability coefficients can be used to calculate whether a blend recipe will be stable or unstable at given time periods.

In another aspect, the invention resides in a system for analysing a blend of two or more hydrocarbon feed streams such as crude oils for processing in a blending facility such as a refinery for assessing the compatibility of a hydrocarbon feed in a blend to calculate the blend stability for assessing the organic deposition from said blend, the system including: apparatus configured to titrate a pseudo-blend with a neat hydrocarbon feed, wherein the neat hydrocarbon feed is the titrant and the or each other hydrocarbon feed is the pseudo-blend; a measurement device configured to measure the change in characteristics of the titrated blend and output the associated measurement data; a processor configured to receive the measurement data, record said data for a plurality of titrations at different blend ratios and calculate the stability of the blend.

A person skilled in the art would appreciate for the teaching of the invention that the system can be configured to implement the methods described herein.

In another aspect, the invention resides in a method of operating a facility for blending hydrocarbon feed streams, or a facility for blending hydrocarbon feed streams.

In another aspect, the invention resides in a computer readable storage medium storing one or more programs, said programs having instructions, which when executed by an electronic system perform a method as claimed.

Using a neat crude that is one of the plurality of hydrocarbon feed streams to be blended, as a titrant, can provide accurate assessments of the blend stability. However, where a refinery uses a large number of different neat hydrocarbon feeds and/or changes the content of the blend frequently (e.g. every 24 hrs) then the time required to make an assessment of the blend stability can become expensive and/or impractical. Therefore, preparing a reference hydrocarbon as a titrant that can be titrated in to a blend of the plurality of hydrocarbon feeds to be included in a blend, and using the aforementioned analysis methods and techniques, reduces the analysis time because fewer test combinations are required.

The term 'feed' refers, by way of example, to a stream or flow of a raw supply of crude oil from an oil production facility such as an oil well. This is typically stored adjacent a refinery and 'fed' in to the blend. Refineries combine a plurality of feeds to form a blend, which is subsequently refined.

A single hydrocarbon 'feed' that has not been mixed, modified or blended since extraction from its source is often referred to as 'neat'. The term 'neat hydrocarbon feed' refers to a hydrocarbon supply from a single source or stock that is representative of a hydrocarbon being streamed in to a blend.

A reference or model hydrocarbon, as referred to herein, is not a 'feed' that is included in a blend. Neither is said reference hydrocarbon a pure solvent such as toluene/1-methylnaphthalene or n-heptane/n-hexadecane. The reference hydrocarbon referred to herein is a combination of selected neat hydrocarbons that, when titrated into a blend of neat hydrocarbon feeds to be processed, allows for an improved assessment of the stability of a blend. In light of the teaching of the present invention, the skilled person would appreciate that aspects of the invention were interchangeable and transferable between the aspects described herein, and can be combined to provide improved aspects of the invention. Further aspects of the invention will be appreciated from the following description.

BRIEF DESCRIPTION OF THE FIGURES

In order that the invention can be more readily understood, reference will now be made, by way of example, to the remaining drawings in which.

DETAILED DESCRIPTION

Figure 1A:
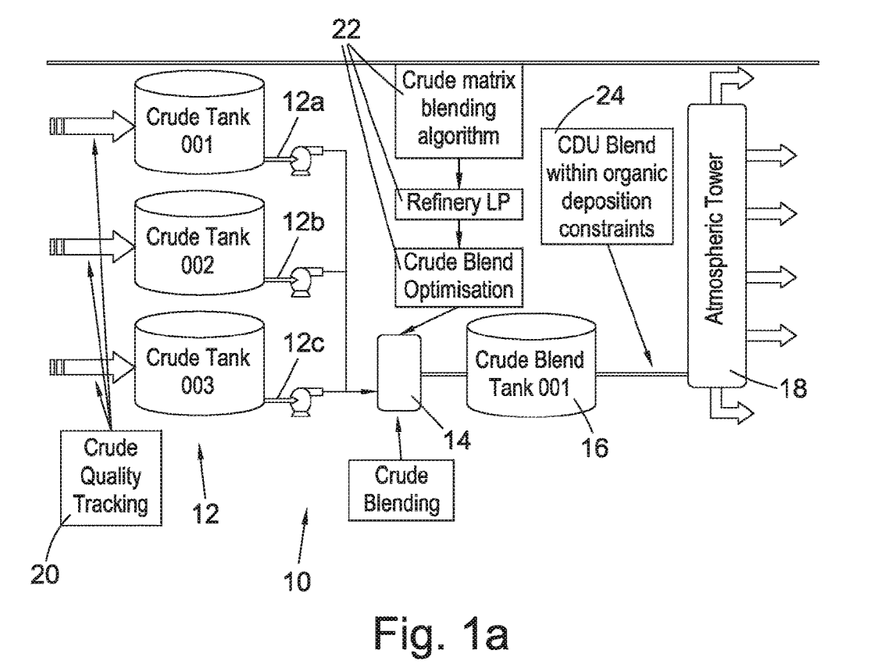
FIGS. 1a and 1b are schematic representations of a refinery system.

In FIG. 1a a refinery system 10, having crude oil holding tanks 12, is arranged to controllably feed crudes to a blender 14 and subsequently hold the blend in a crude store or blend tank 16. The output 12a, 12b, 12c from each tank is referred to as the 'feed', which comes from a raw supply of crude oil from an oil production facility such as an oil well that is held in each tank. Each feed 12a, 12b and 12c is combined to form a blend that is fed to the blend tank 16. The store feeds an atmospheric tower 18. Measurement systems 20 monitor the quality of each crude. Physical and/or theoretical calculations 22 are performed to determine the percentage of crude in the blend. The resulting feed to the Crude Distillation Unit (CDU) 24 is prepared to meet refinery operating conditions e.g. organic deposition constraints.

Overall, OD is defined as flocculation and precipitation of organic substances such as asphaltene and other crystalline organic material can occur when crude oils are blended. The invention provides a means of assessing OD based on the blending of crude oils from an individual refinery crude slate. OD is characterised over different time periods, from initial blending time to an extended storage time as experienced in a refinery. The invention uses known measurement technologies, such as near Infrared (NIR) spectroscopy and microscopy, when measuring properties of crude oils and blends of crude oils. Measurement data is used to establish chemometric models of crude oils for near neighbour analysis and spectral distance analysis. Spectra are used to detect both chemical composition and organic deposition.

The means of the invention use apparatus and methods to analyse the blend stability to minimising the organic deposition from said blend. The techniques include:

A. Quality tracking, in which the properties of neat crude are measured.

B. Establishing and recording blend feasibility reports and recipes according to available ingredients for the blend and refinery constraints.

C. Measuring and evaluating blends using all of a plurality of hydrocarbon feeds that are to be included in a blend for processing and either using a neat crude as a titrant and titrating said neat crude into a pseudo-blend comprising the remaining crudes in the blend, or using a reference hydrocarbon as a titrant for titration into a blend of the plurality of hydrocarbon feeds.

D. Evaluating a blend, and reporting the same, using blend stability and instability coefficients to identify whether a blend will be stable, and whether said blend will be stable over a period of time, and updating the feasibility report (B) with the results of blend evaluations.

E. Validating a sample blend or a measured blend through comparison with the results of blend experiments, such that the difference therebetween can be used to indicate the probability of organic deposition.

Figure 1B:
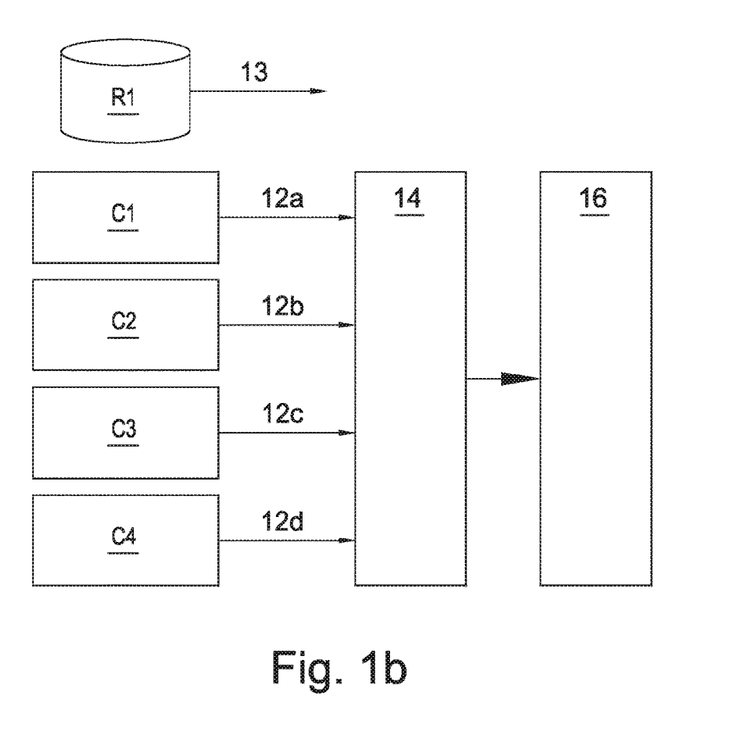

A simplified representation of the main elements of a refinery system 10, as shown in FIG. 1a, is shown in FIG. 1b, wherein the different sources of neat hydrocarbon feed, or crudes available from the refinery slate are represented. Each holding tank 12 is shown having different crudes—C1, C2, C3 and C4—which provide feeds 12a, 12b, 12c 12d to a blend stage 14 that results in a blend 16. A reference hydrocarbon R1 is also shown providing a reference feed 13.

Analysis using a neat crude as a titrant and the remaining crudes as a pseudo-blend involves analysis combinations as shown in the table below:

| Analysis combinations. Crudes available: C1, C2, C3 and C4 | | | |
|---|---|---|---|
| Titrant | Pseudo-blend comprises: | | |
| C1 | C2 | C3 | C4 |
| C2 | C1 | C3 | C4 |
| C3 | C1 | C2 | C4 |
| C4 | C1 | C2 | C3 |

Analysis using a reference hydrocarbon R1 and a reference feed 13 therefrom as a titrant can require fewer measurements while still providing for a more efficient assessment means of assessing organic deposition from a blend.

Analysis using a reference crude as a titrant, which is titrated in to a blend having selected neat hydrocarbon feeds C1, C2, C3 and C4, is shown in the table below:

| Analysis combinations. Crudes available: C1, C2, C3 and C4 | | | | |
|---|---|---|---|---|
| Titrant | Blend composition: | | | |
| R1 | C1 | C2 | C3 | C4 |

In light of the teaching herein, the skilled person would appreciate that the invention resides in calculating the stability of a blend of hydrocarbon feeds. The core technique, namely "C", uses all of the neat hydrocarbon feeds that a refinery intends to blend and process. In this way a more accurate assessment of the blend stability can be made.

Analysis is carried out using near infrared (NIR) spectra measurements and mathematical modelling algorithms, such as regression analysis. Crude blends are assessed, measured and blend stability coefficients are calculated and compiled in a blend recipe evaluation report.

As opportunity crudes and load port samples become available these are assessed and then added to the blend feasibility report. Feasible blends are verified using a neat crude, or a reference crude, as the titrant.

The assessment of OD is based on blending refinery neat crude oils. Therefore the assessment is representative of actual refinery operating parameters and the experimental measurements reveal the interaction between crudes during and after blending. Analysis through assessing, measuring and/or calculating includes one or more of, IR/NIR Spectroscopy—using FT-IR/FT-NIR spectrometers between 485 $cm^{-1}$ (21 um) to 10,000 $cm^{-1}$ (1000 nm)

Microscopy
Calculation using a Blending Algorithm
Blend Stability Coefficient (BSC)
Blend Instability Coefficient (BIC)
Spectral Blending Algorithm
Quality Tracking (Fingerprinting)

The analysis assesses the response over time and multiple samples are stored, NIR scanned and validated by microscopy and mathematical calculations. A programme, or analysis method, includes at least one of:

A Blend Feasibility Report.
A summary of blend recipes that meet the refinery constraints.
A summary of neat crude properties.
Calculated blend properties.

Experimental results from blend titrations provide at least one of:

A summary of recipes evaluated.
The stability/instability of a blend validated by at least one of NIR measurement, observation or calculation.

The blend evaluation report provides the Blend Stability Coefficient (BSC) and Blend Instability Coefficient (BIC). These coefficients are derived from experimentation, observation and regression analysis. In more detail, the techniques are described below:

Matrix Blending Process

Overall, the invention provides a means and/or method of assessing the stability of crude blends. The process can include a number of techniques, such as those disclosed below (i.e. techniques A to D). To begin, an assessment of refinery crude blends is made. The output is an assessment of the stability of a blend that a refinery operator wants to prepare.

Quality Tracking—Technique A

Neat crude is measured and assessed for quality, composition and organic deposition together with true boiling point (TBP) and whole crude properties. The assessment includes NIR Scanning, Property Prediction, Aggregate Assessment, nearest neighbour analysis and spectral distance.

Aggregates have been developed based on both spectral and property correlations, including but not limited to density, paraffins, napthenes and aromatics (PNA), total acidic number (TAN) and sulphur.

Crude qualities vary between batches; variation is normally by API and Sulphur checks. The combined solution utilises NIR and calculations to track and monitor crude quality. NIR fingerprinting takes account of crude quality change, thus giving the refiner a 'heads up', or an early indication, on neat crude deliveries and the potential effects any change has on a blend. If appropriate an assessment of compatibility of the neat crude samples within a blend can be undertaken the refiner can ensure the actual blend recipe used meets current refinery constraints.

Each neat crude is scanned using NIR between the wave numbers 4000 $cm^{-1}$ (wavelength 2500 nm) and 10000 $cm^{-1}$ (wavelength 1000 nm). Quality tracking uses data from measurements taken in the combination region (4000 to 4800 $cm^{-1}$). The measured values are compared against values predicted by NIR within a chemometric model. Calculations assume that a neat crude of a given quality has the same effect on the blend providing the quality remains constant. Monitoring the quality allows assessments to be made if neat crude quality changes. If a change is detected the effect of that neat crude on the blend is re-assessed.

Figure 2:
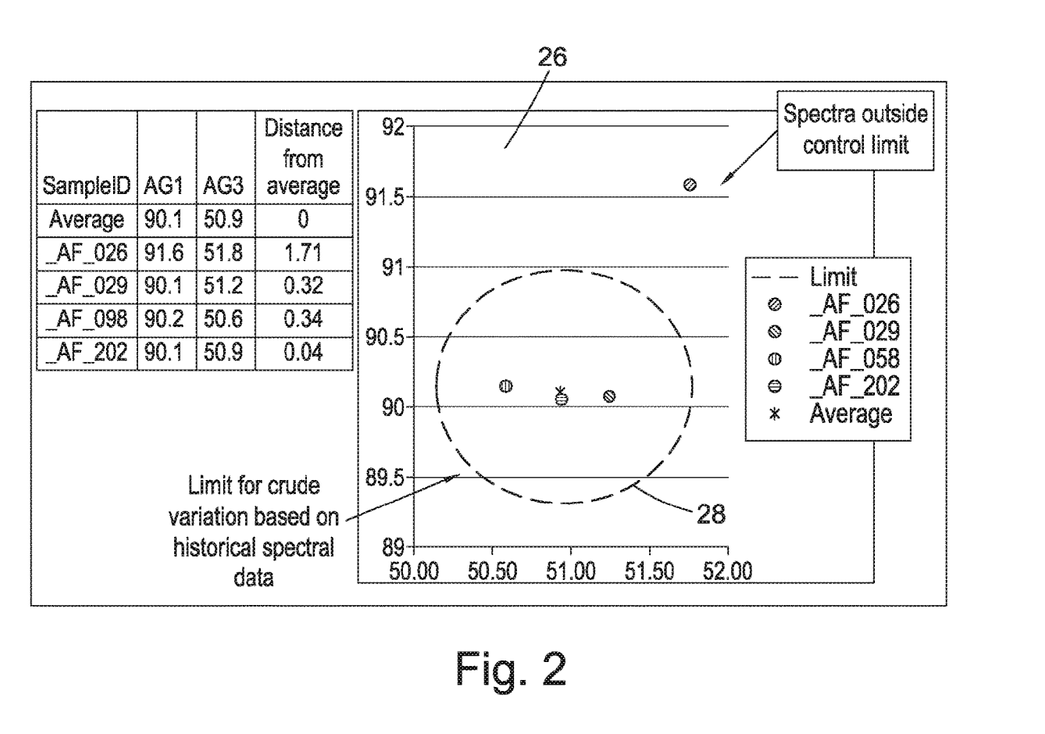
FIG. 2 is a graphical assessment of the properties of a number of crude oils.

FIG. 2 shows a plot 26 of the results of measurements and calculations taken for a selection of crude oils. New measurements are taken and assessed against a threshold 28 representing, by way of example, a 95% confidence ellipse (indicated by the dashed line, as shown). Such outliers are assessed based on their deviation from average measurements. If the measurement result of a neat crude scan lies outside this threshold then said crude is reassessed, and the blend feasibility report (see technique B, below) is updated to indicate feasible blends.

NIR spectra allow finger printing of neat crudes and provide an assessment of changes in neat crude composition. Assessment is made using calculations, near neighbour analysis, spectral distance analysis and aggregates.

Figure 3:
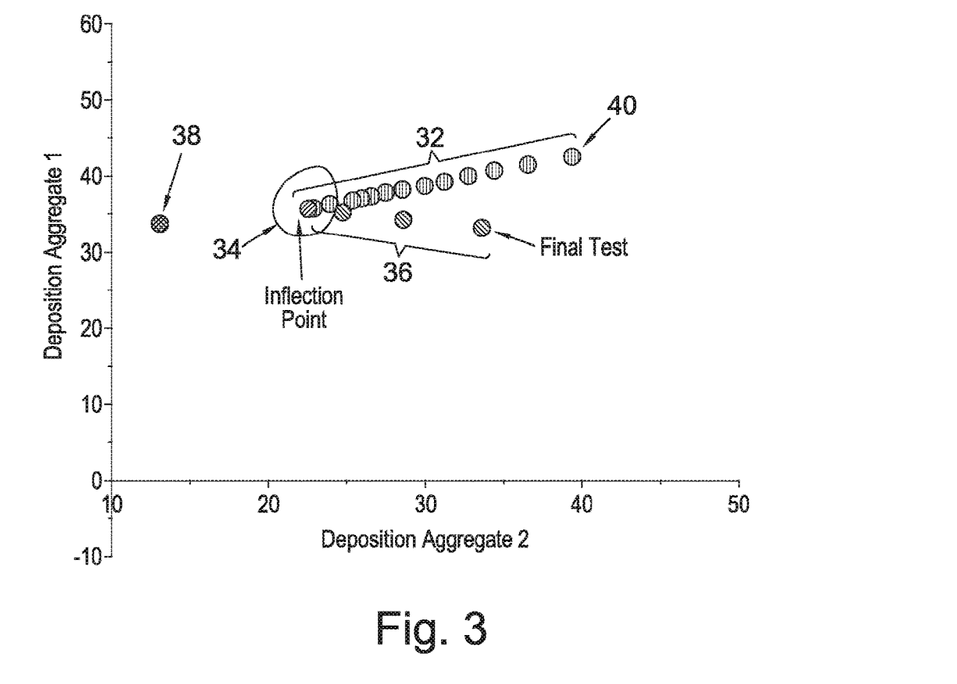
FIG. 3 is a graph plotting NIR measurements and the inflection point at which Organic Deposition (OD) occurs during titration.

OD is observed by a NIR spectral inflection point, as shown in FIG. 3. This spectra is measured over time during the titration to determine the inflection point. This can be characterised by three (3) phases 32, 34, 36 that can be compared against the spectra of the titrant crude oil 38 and the pseudo component blend 40. In the first phase 32, starting from the first blend test, spectra blend linearly and as a crude is titrated the spectra moves towards the titrant as indicated by the arrow. In the second phase 34, the onset of OD at an inflection point is observed. In the third phase 36, the increase in titrant results in the spectral trajectory deviating from the expected behaviour as indicated by the arrow.

Figure 4:
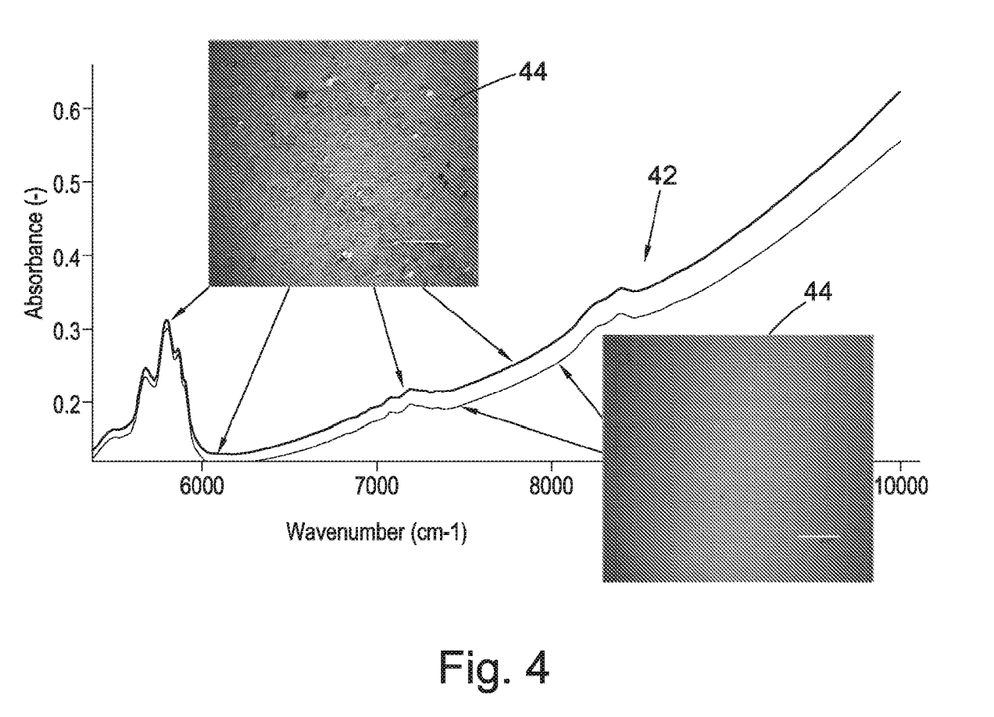
FIG. 4 is another graph showing a spectral inflection and associated pictures of microscopy validation.

FIG. 4 shows two NIR measurement readings showing the spectral behaviour at two different instances in the titration. Due to scattering of light by particle flocculation the absorbance increases throughout the whole spectrum (3880 $cm^{-1}$ to 10000 $cm^{-1}$). Chemical changes due to OD are also observed in the 3800 $cm^{-1}$ to 4800 $cm^{-1}$ region (known as the combination region). Images 44 of microscopy pictures validate the change in spectral behaviour.

For quality tracking purposes, the aggregate plot is prepared from the combination region. The spectra used is both pre-processed and normalised to remove effects of particulates and water. The sample spectra is checked to see if the properties of a neat crude to be blended fall within the range of the historical cluster of samples (e.g. within the threshold 28) for comparable neat crudes of the same type or family. If the spectrum varies and indicates, for example, that the density and sulphur measurements have deviated then further analysis is required and the blend feasibility report updated. Similarly, if a new crude of a type not previously assessed is to be blended then the blend feasibility report is updated.

Blend Feasibility Report—Technique B

Crude blends recipes are identified by the refiner according to the current refinery operating conditions and crude delivery schedule. The crude blend constraints from the refinery plan, production units and crude slate limit the actual crude blending options available to a refinery planner.

A refinery operator uses current refinery operating constraints and then identifies blend recipes that meet current refinery operating constraints. A series of blend experiments which cover the range of refinery blending operations is established using neat crudes. Recipe clusters are established using a blend feasibility report (see FIG. 5). These experiments take into account the practical minimum and maximum percentage volumes of a neat crude that is to be added to a blend.

Differences in neat crude quality is monitored and neat crudes selected to make up refinery blends, both feasible and infeasible, based on individual refinery constraint sets, to ensure the refinery operating envelope is captured.

Figure 5:
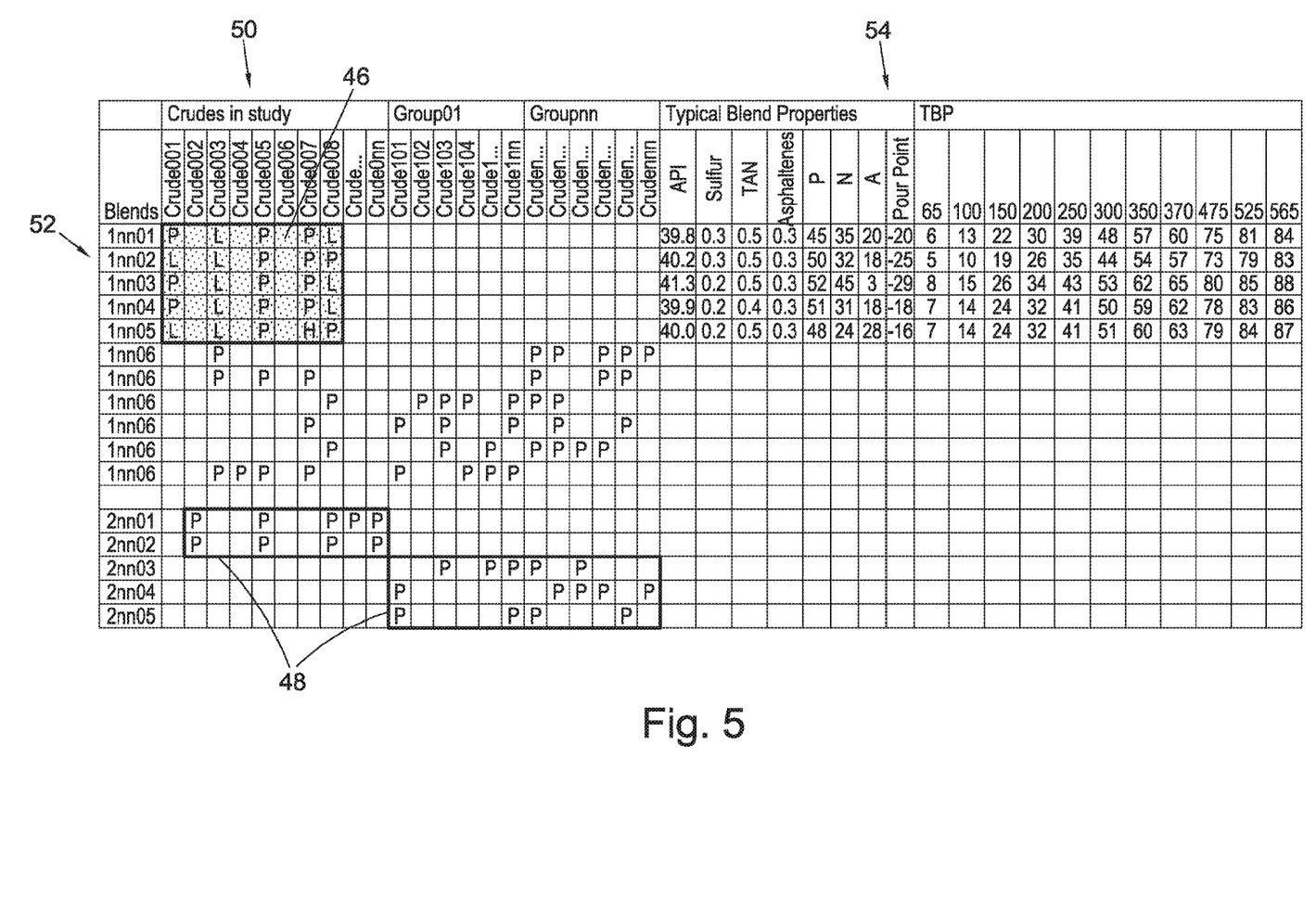
FIG. 5 is a table showing which crude oils can be feasibly added to a blend.

For each crude blend an assessment based on NIR spectra, typical blend properties and refinery constraints is made. The results are used to establish a blend feasibility report, as shown in FIG. 5. Crudes that can be blended together to meet the blend constraints are populated as follows: P, possible blend component; L, low percentage blend component; H, high percentage blend component and X, infeasible blend.

The report is populated in stages as new neat crude samples become available, and the report is updated as blending constraints are updated. In the report, analysed results 46 are recorded to indicate whether crudes can be blended. Possible (P) blends 48 indicate blends that will need to be checked and evaluated based on NIR spectra, typical blend properties and constraints. Blend components assessed to be infeasible are marked on this table. Each of the potential blend recipes can be assessed using technique C below, and this report can be updated with the results accordingly.

The table shows the following: neat crudes to be added to a blend, listed as columns 50; potential blend recipes listed as rows 52, grouped by CDU blend types; and typical blend constraint properties 54 are shown on the right hand side of the table.

As will be appreciated, the experimental results and calculations from the blend recipe evaluation report are provided by a feedback loop to update said blend reports for target CDU recipes. The blend evaluation reports account for the following:

A summary of blend recipes that meet the refinery constraints.
A summary of neat crude properties.
Calculated blend properties.
Range of percentage of crudes blended.
Minimum percentage.
Maximum percentage.
Average percentage
Span percentage Overall, the refinery process is analysed to provide blend recipes that match the current refinery operating constraints. This identification of the range of feasible blends provides boundaries. Blend recipes that lie at the perimeter of a refineries operating envelope can be selected for the blend titration (as per technique C below). Blend titrations are, however, carried out over both feasible and infeasible blend regions. The calculated stability of feasible and infeasible blends, and those borderline blends, allows accurate blending and optimised selection of neat crudes for use in a blend. By measuring and calculating in the borderline region the risk of a blend not meeting refinery constraints (and resulting in organic deposition) can be reduced. By improving the accuracy of the report the risk of organic deposition can be reduced such that a maximum amount of a neat crude can be added to a blend while continuing to operate within refinery margins. This can be to enable, for example, a maximum amount of a low cost crude to be added to a blend such that the overall cost of the blend is reduced without increasing the risk of organic deposition.

Blend Titration—Technique C

To assess whether adding a neat crude will influence the stability of a blend all of the neat hydrocarbon feeds that a refinery intends to blend and process are used when measurements are taken for analysis.

Figure 6:
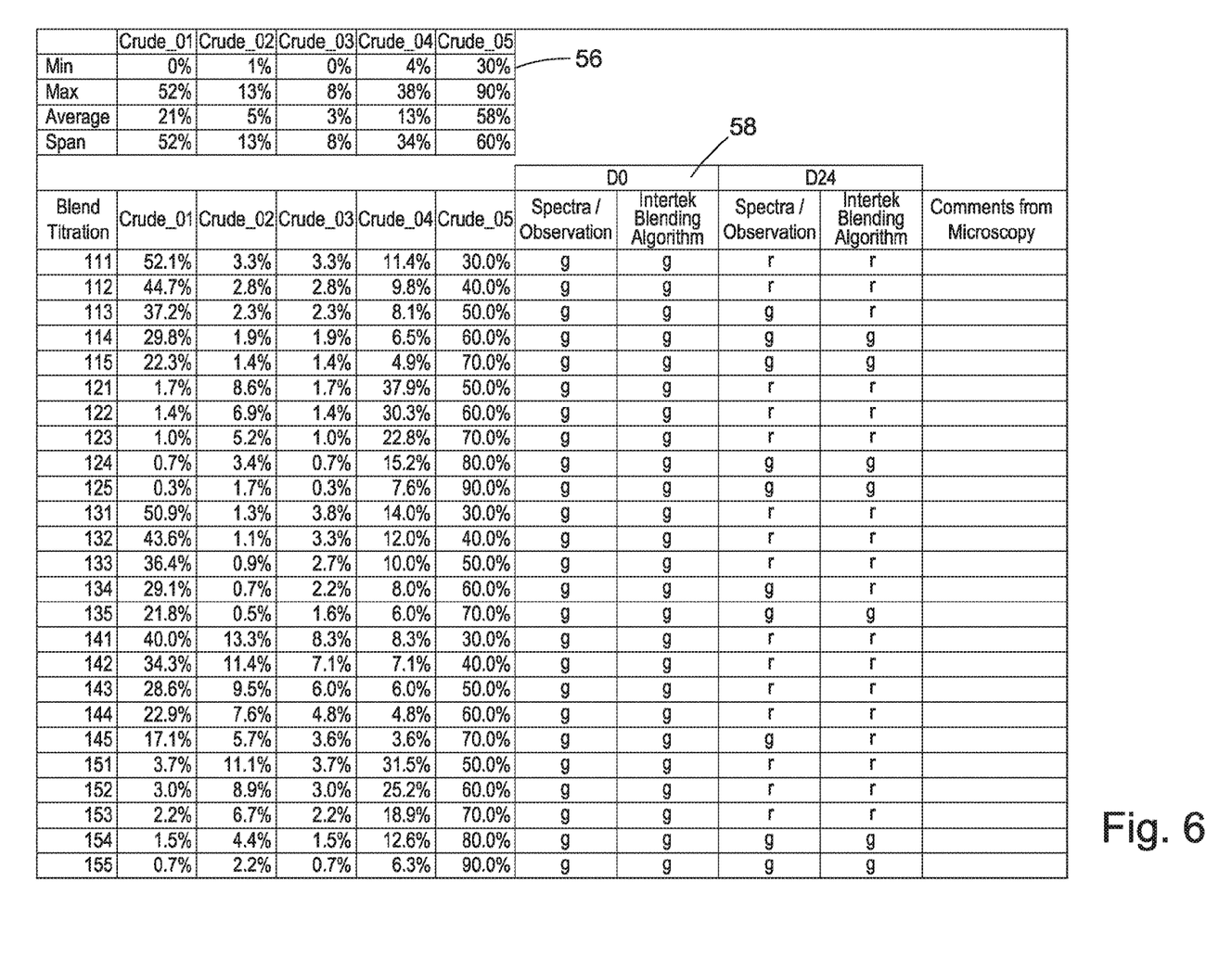
FIG. 6 shows tables that summarise experimental blend titration results.

One of the crudes in a blend recipe is selected a titrant, which is then titrated into a series of feasible and infeasible pseudo component blends, composed of the remaining neat crudes (or pseudo-blend). The titrant crude is selected based on aggregate assessment, spectral distance and properties. The pseudo-blends are then titrated with the neat crude titrant to cover regions of stability and instability. This gives the point of blend instability in terms of neat crude ratios in the refinery target crude blends. The stability/instability by NIR measurement, observation, and calculation are assessed at different time periods. The observed organic deposition and the organic deposition are shown in FIG. 6, which tabulates the experimental results from a series of blend titrations. An upper table 56 indicates the range of percentages of the neat crudes in the blends, including Minimum, Maximum Average and Span. The lower table 58 shows the percentage crude blend at each of the steps of the crude titrations, the detection of organic deposition by spectra at time 0 hrs (D0) and at +24 hrs (D24), the prediction of organic deposition from experimental blending coefficients, and observations from microscopy. A 'g' in the table indicates a 'green' or positive result i.e. a feasible blend, while 'r' indicates a 'red' or negative result i.e. an infeasible blend. In the lower table 58, 'Crude_05' has been selected as a titrant. Each row in the table represents a different blend recipe. Through a series of titrations the onset of organic deposition is measured for different recipes. Pseudo component blends and titrant levels are determined by the blend feasibility report. Titrations are then performed using discrete samples. By way of example, one vial for each day of analysis is used for spectroscopy and microscopy measurements).

The blend titrations are observed by using NIR spectra across the full range of 4000 cm-1 (wavelength 2500 nm) to 10000 cm-1 (wavelength 1000 nm) to observe the onset of deposition. The point of deposition is directly related to a NIR spectral inflection point. The change in NIR spectra measurements due to the deposition of organic material provides multivariate data, which can be analysed using mathematical regression analysis techniques. Data analysis covers the region of 4000 $cm^{-1}$ to 10000 $cm^{-1}$. Using the whole spectra allows changes in both physical and chemical composition to be observed. A true inflection point exhibits a distinct increase in absorbance throughout the whole spectrum. This can be represented by the difference between the lines show on the graph of FIG. 3.

Multivariate mathematic calculations are used to assess the crude blend titrations and provide coefficients for neat crudes which can be used to make assessments of compatibility of these crudes when blended.

Figure 7:
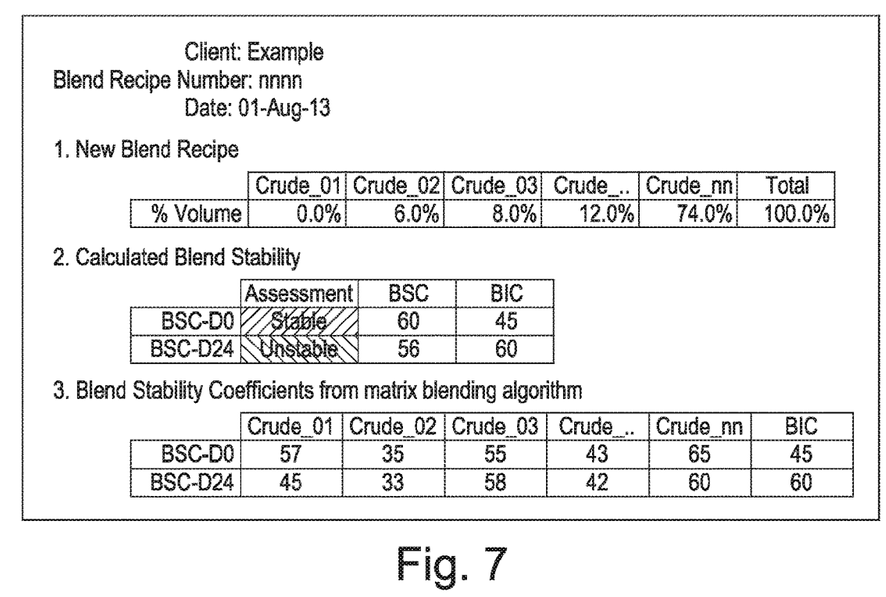
FIG. 7 shows tables indicating blend stability.

Alternatively, a reference hydrocarbon R1 and the reference feed 13 therefrom is used a titrant, which is titrated in to a blend of all of the hydrocarbon feeds 12*a*, 12*b*, 12*c*, 12*d* that a distillation facility intends to blend. Blend Evaluation Report—technique D Coefficients calculated from the results of the titrations shown in FIG. 6 are used to generate a set of reports for target blend recipes indicating whether a blend will be stable or unstable at given time periods. This blend evaluation report is shown in FIG. 7, and the three tables contained within the report are as follows.

To calculate the coefficients for each crude in the blend, the inflection points of the blend titration are taken with the pseudo-blend component ratios at the point of inflection for each blend as the X block and the corresponding titrant level is the Y block. A regression analysis is performed to acquire coefficients for each of the blend components which reflect the point of organic deposition for all ratios tested. These coefficients can then be proportionally factored or blended using the blend evaluation report to ascertain whether a selected blend ratio is stable or unstable. The onset of OD is input into, by way of example, a regression analysis to calculate said coefficients.

Regression analysis is used to calculate the stability coefficient for each crude in the blend. This coefficient is multiplied by the percentage volume (%) of said crude in the blend. The result is summed to provide the overall Blend Stability Coefficient (BSC). The BIC is derived, mathematically, from the BSC (see Equation 1)

Table 1 includes a new blend recipe indicating the percentage volume of the crudes in the blend. The percentage volume of each crude in this blend can be changed to evaluate changing blend recipes for organic deposition. The degrees of freedom of the volume percentages of the individual crudes are limited by refinery operating conditions.

Table 2 includes blend stability assessment indicating the blend recipe stability at 0 h (D0) and +24 h (D24). If the Blend Stability Coefficient (BSC) at 0 hrs. (60 for this blend recipe of crudes) is greater than Blend Instability Coefficient (BIC) (45 for this group of crudes) then the blend is stable at 0 hrs. If the Blend Stability Coefficient (BSC) at 24 hrs. (45 for this blend recipe of crudes) is less than Blend Instability Coefficient (BIC) (60 for this group of groups) then the blend is unstable at 24 hrs.

Table 3 includes the calculated Blend Stability Coefficients of each of neat crude within the blend. The Blend Stability Coefficients and Blend Instability Coefficients are constants for this set of crudes and are obtained from the results of the titrations A Blend Stability Coefficient (BSC) and Blending Instability Coefficient (BIC) are calculated to quantify the effect of neat crude interaction at different temperatures and/or or a period of time, e.g. at intervals between 0 hrs. and +24 hrs. These titrations are carried out to mimic refinery storage and processing conditions.

Using multivariate mathematics, blend stability coefficients (BSC) and instability coefficients (BIC) are determined from the experimental results shown in FIG. 6.

Using BSC and BIC coefficients for neat crudes in a recipe cluster (see technique C) the practical minimum and maximum percentage volume can be calculated. These percentage volume ranges are used to design a series of blend experiments which cover the range of refinery blending. For each blend experiment a titrant is chosen that will make the blend go from stable to unstable. The remaining neat crudes are blended into a pseudo component to be used with the titrant crude.

TABLE 1

Example Blend Experiment

| Blend | Crude_01 | Crude_02 | Crude_03 | Crude_04 | Crude_05 |
|---|---|---|---|---|---|
| 110 | 74.4% | 4.7% | 4.7% | 16.3% | 0.0% |
| 111 | 52.1% | 3.3% | 3.3% | 11.4% | 30.0% |
| 112 | 44.7% | 2.8% | 2.8% | 9.8% | 40.0% |
| 113 | 37.2% | 2.3% | 2.3% | 8.1% | 50.0% |
| 114 | 29.8% | 1.9% | 1.9% | 6.5% | 60.0% |
| 115 | 22.3% | 1.4% | 1.4% | 4.9% | 70.0% |

In Table 1 above, example blend experiments are listed, showing:
The pseudo component is blended for the experiment (e.g. blend 110).
Vials of the pseudo component are combined with different percentage volumes of the titrant crude (i.e. Crude_05).
The vials are scanned and the NIR-spectra are monitored to and identifies when OD has occurred.
The initial screening series of vials uses large increments of titrant (e.g. 10%).
To fine tune the point of OD, after screening with large increments, smaller increments are used (e.g. 1%).
The vials are scanned following mixing and after one or more retention times (e.g. 0 hrs.+24 hrs.).
Duplicate vials are available for microscopy and laboratory analysis which can be selectively triggered based on the information obtained from the assessment from the NIR spectra.

Regression—Calculating the Coefficients

At the point of organic OD the following assertion can be made:

$$eBIC = eBSC_0 V_0 + eBSC_1 V_1 + eBSC_2 V_2 + \ldots + eBSC_n V_n \quad \text{Equation 1}$$

Where
eBIC Experimental blend instability coefficient
$eBSC_n$ Experimental blend stability coefficient for component n
$V_n$ Percentage volume of component n
Rearranging in the form $$V_0 = \beta_0 \beta_1 V_1 + \ldots + \beta_{n-1} V_{n-1} \quad \text{Equation 2}$$

Where
$V_0$ volume of titrant
$\beta_0 \ldots \beta_n$ Constants
$\beta_0$ IC−(SC$_0$−SC$_n$)
$\beta_{n-1}$ SC$_n$−SC$_{n-1}$(SC$_0$−SC$_n$)
SC$_n$ IC−$\beta_0$SC$_0$(1−$\beta_0$)
SC$_{n-1}$ SC$_n$−$\beta_{n-1}$(SC$_0$−SC$_n$)

A matrix solution to the least squares fit which gives a solution for the coefficients for this range of neat crude blends for refinery organic deposition.

$$B^{\wedge}(V'V - 1V'Y) \quad \text{Equation 3}$$

Where
$B^{\wedge}$ Regression coefficients $\beta_0 \ldots \beta_n$
Blending and Regression Fitting Having obtained the experimental data from the blend titration mathematical regression analysis can be used to enable the stability of any crude ratio in a blend recipe to be calculated. The confidence in the regression can also be calculated to ensure that sufficient, repeatable measurements have been made in the blend titrations.

Blend Validation—Technique E

Figure 8:
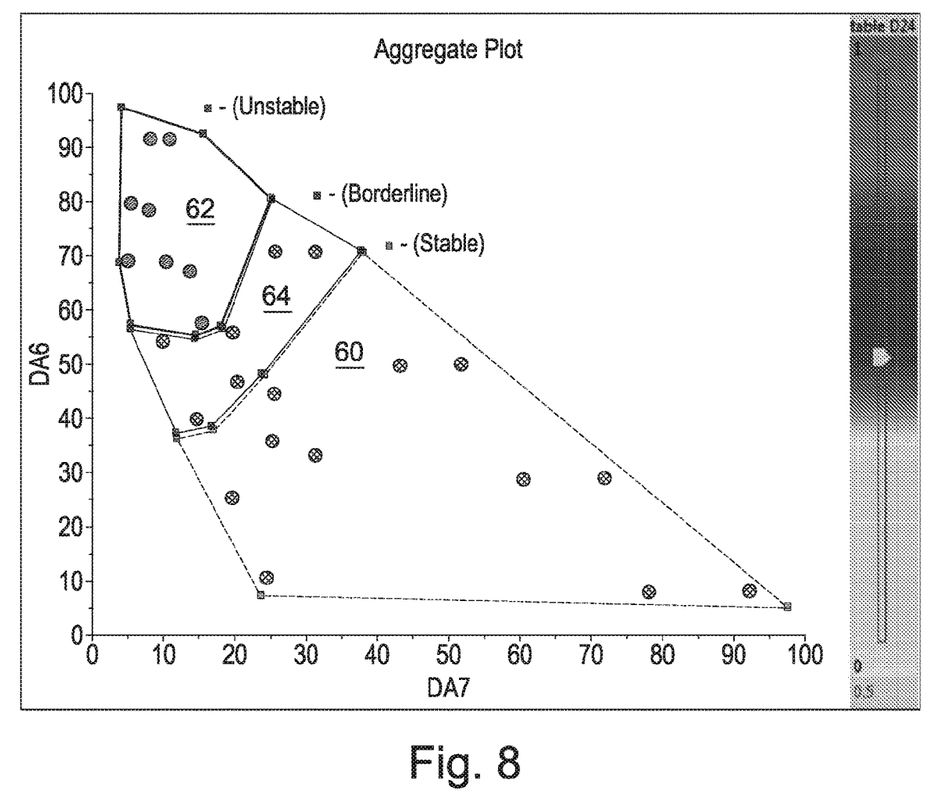
FIG. 8 is an aggregate plot indicating the stability of a blend.

Assessment of blend stability and instability also allows plots to be constructed with axes based on functions of absorbance at selected key wavenumbers; these plots are known as aggregate plots. FIG. 8 is an aggregate plot with regions of stability 60 and instability 62, with borderline areas 64 therebetween. These areas of blend stability and the boundaries are determined from experimental blend assessments. These boundaries can be calibrated regularly.

The spectra of neat crudes allow theoretical blended spectra properties to be calculated using different mixing rules within the chemometric model. Calculated samples are compared to spectra obtained from actual blend experiments and refinery operation. The difference between theoretical blends and actual blends is used to assess the stability of a blend and the probability of organic deposition. The aggregate plot takes in to account: neat crude spectra; spectra from crude blend titrations; pseudo component spectra; titrant crude spectra; and actual crude spectra from the blend header. Using these plots, regions of stability 60 and instability 62 can be defined graphically, allowing an operator of a refinery system to take NIR scans of blends and make assessments of blend stability.

Using the techniques of the invention and a database of crudes and their characteristics the invention enables a refinery operator to predict physical properties of crude. To predict the properties laboratory analysis is required to tune a model. Once the model has been tuned the predictions can be made for every neat crude delivery.

Characteristics are derived from NIR spectra analysis and comparison of: neat crude spectra; spectra from crude blend titrations; pseudo component spectra (i.e. crude blend before addition of titrant crude); titrant crude spectra; and actual spectra from blend header (optional).

In other words, a refinery operator can prepare a blend that he wishes to process. The blends available to him will be determined by the slate and the operating conditions, such as the operating facilities of the refinery. The NIR spectra of said blend is measured and plotted on the aggregate plot. The aggregate plot is populated with the NIR spectra of blends whose stability is known from experiments according to the present invention. The refinery operator can then assess the position of the blend he wishes to process with the defined regions 60, 62, and 64. In this way, the operator can take NIR scans of blends and make assessments of blend stability. The difference between the desired blend and the measured blends can be used to assess the probability of organic deposition. This assessment can be verified using the above mentioned method.

Figure 9:
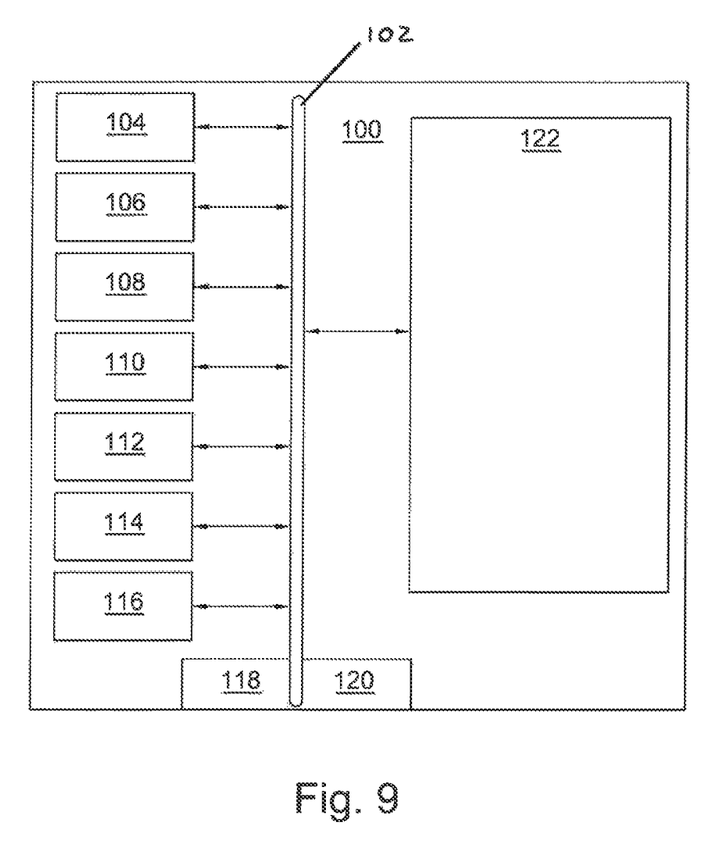
FIG. 9 is a schematic representation of a device configured to implement the invention

By way of example, the method of the invention can be implemented on a device 100 having the components shown FIG. 9, which is an example of a computer system. The device 100 includes a bus 102, at least one processor 104, at least one communication port 106, a main memory 108, a removable storage media 110, a read only memory 112 and a random access memory 114. The components of device 100 can be configured across two (2) or more devices, or the components can reside in a single device 10. The device can also include a battery 116. The port 106 can be complimented by input means 118 and output connection 120.

The processor 104 can be any such device such as (but not limited to) an Intel®, AMD® or ARM processor. The processor may be specifically dedicated to the device. The port 106 can be a wired connection, such as an RS-232 connection, or a Bluetooth connection or any such wireless connection. The port can be configured to communicate on a network such a Local Area Network (LAN), Wide Area Network (WAN), or any network to which the device 100 connects. The read only memory 112 can store instructions for the processor 104.

The bus 102 communicably couples the processor 104 with the other memory 110, 112, 114, 108 and port 106, as well as the input and output connections 118, 120. The bus can be a PCI/PCI-X or SCSI based system bus depending on the storage devices used, for example. The removable memory 110 can be any kind of external hard-drives, floppy drives, flash drives, for example. The device and components therein is provided by way of example and does not limit the scope of the invention. The processor 104 can implement the methods described herein.

The processor 104 can be configured to retrieve and/or receive information from a remote server or device.

The device 100 also includes a user interface 122, to receive commands which may have been input via, for example but not limited to, a touch sensitive device, a joystick or transducers The present invention has been described above purely by way of example, and modifications can be made within the spirit and scope of the invention, which extends to equivalents of the features described and combinations of one or more features described herein. The invention also consists in any individual features described or implicit herein.

The invention claimed is:

1. A method for analysing a blend of two or more hydrocarbon feed streams for processing in a blending facility for assessing the compatibility of a hydrocarbon feed in a blend to calculate the blend stability for assessing organic deposition from said blend, the method including:
    using all of a plurality of hydrocarbon feeds to be blended for analysis;
    preparing a reference hydrocarbon and making a blend from the plurality of hydrocarbon feeds;
    titrating the blend with the reference hydrocarbon as a titrant;
    measuring and recording data associated with the change in characteristics of the titrated blend; and
    calculating, using said data, the stability of the blend,
    wherein the properties of two or more hydrocarbon feed streams are selectable from a dataset having a record of the properties of each hydrocarbon feedstream,
    wherein the dataset includes a list of feasible and infeasible blends for a blending facility, and
    wherein the method monitors the characteristics of the or each hydrocarbon feed stream and, if the measured characteristics of a hydrocarbon feed stream fall outside a control limit, or a new hydrocarbon feed is to be included in the dataset, said hydrocarbon feed is selected as the titrant.

2. A method according to claim 1, wherein the plurality of hydrocarbon feeds selected for a blend, and the titrations therefrom, use discrete samples to simulate refinery storage and processing conditions.

3. A method according to claim 1, wherein the plurality of hydrocarbon feeds selected for a blend are selected to identify stable and unstable blends that overlap or extend beyond a refinery operating envelope.

4. A method according to claim 1, wherein a series of titration experiments are carried out and blend stability is calculated from regression analysis on the data.

5. A method according to claim 4, wherein the data includes the point of organic deposition of the blend titration and the associated ratio of each component of the blend and the titrant level.

6. A method according to claim 4, wherein regression analysis is used to calculate a coefficient for each hydrocarbon feed of the blend.

7. A method according to claim 6, wherein a series of titration experiments are carried out for stable and unstable blend recipes and spectra measurements taken at the point of organic deposition for each blend are mapped on an aggregate plot such that the differences therebetween are calculated to validate the coefficient.

8. A method according to claim 1, wherein stability and instability coefficients are used to calculate whether a blend recipe will be stable or unstable and/or stable or unstable at given time periods after the titration.

9. A system for analyzing a blend of two or more hydrocarbon feed streams for processing in a blending facility for assessing the compatibility of a hydrocarbon feed in a blend to calculate the blend stability for assessing organic deposition from said blend, the system including:
    apparatus configured to utilize all of a plurality of hydrocarbon feeds to be blended for analysis and titrate a blend of the plurality of hydrocarbon feeds with a reference hydrocarbon, wherein the reference hydrocarbon is the titrant and the blend is prepared from the plurality of hydrocarbon feeds;

a measurement device configured to measure the change in characteristics of the titrated blend and output the associated measurement data;

a processor configured to receive the measurement data, record said data for a plurality of titrations at different blend ratios and calculate the stability of the blend;

wherein the properties of two or more hydrocarbon feed streams are selectable from a dataset having a record of the properties of each hydrocarbon feedstream, wherein the dataset includes a list of feasible and infeasible blends for a blending facility, and wherein the system monitors the characteristics of the or each hydrocarbon feed stream and, if the measured characteristics of a hydrocarbon feed stream fall outside a control limit, or a new hydrocarbon feed is to be included in the dataset, said hydrocarbon feed is selected as the titrant.

10. A computer readable storage medium storing one or more programs, said programs having instructions, which when executed by an electronic system perform a method according to claim 1.

* * * * *